United States Patent [19]

Spes et al.

[11] Patent Number: 5,231,206
[45] Date of Patent: Jul. 27, 1993

[54] CYCLIC ORGANOSILOXANES HAVING NONLINEAR OPTICAL PROPERTIES

[75] Inventors: Peter Spes, Munich; Mechthild HeBling, Unterföhring; Franz-Heinrich Kreuzer, Martinsried, all of Fed. Rep. of Germany

[73] Assignee: Consortium fur elektrochemische Industrie GmbH, Munich, Fed. Rep. of Germany

[21] Appl. No.: 617,226

[22] Filed: Nov. 23, 1990

[30] Foreign Application Priority Data

Dec. 5, 1989 [DE] Fed. Rep. of Germany ....... 3940148

[51] Int. Cl.$^5$ ............................ C07F 7/04; C07F 7/08; C07F 7/21
[52] U.S. Cl. ..................................... 556/413; 556/415; 556/425; 556/436; 556/437; 556/438
[58] Field of Search ............... 556/413, 415, 425, 436, 556/437, 438

[56] References Cited

U.S. PATENT DOCUMENTS 4,801,659  1/1989  Leslie ................................... 556/413

FOREIGN PATENT DOCUMENTS 0243806  11/1987  European Pat. Off. .

OTHER PUBLICATIONS

Percec et al, J. Polym. Sci., Part A: Polym Chem. 27(7) 2367–84.

Primary Examiner—Jose' G. Dees
Assistant Examiner—Joseph M. Conrad

[57] ABSTRACT

Cyclic organosiloxanes which contain at least one Si-bonded organic radical and have at least one donor/acceptor $\pi$-electron system.

22 Claims, No Drawings

CYCLIC ORGANOSILOXANES HAVING NONLINEAR OPTICAL PROPERTIES

The invention relates to cyclic organosiloxanes and more particularly to cyclic organosiloxanes having nonlinear optical properties, a process for their preparation and their use.

BACKGROUND OF THE INVENTION

Nonlinear optics involves the interactions of electromagnetic fields in various materials which cause new fields of modified phase, frequency, amplitude or other propagation characteristics to be produced. In the area of microelectronics (optical switches, integrated circuits, frequency doubling or trebling) and communications technology, there is great interest in finding materials in which these effects occur.

Whereas, inorganic crystals, such as lithium niobate and gallium arsenide, or organic crystals, such as urea, have received attention in the past, polymeric materials having a donor/acceptor-substituted, delocalized $\pi$-electron system are preferred today. In addition to the easier processibility of polymeric materials, an essential advantage is the possibility of obtaining thin, transparent films. In these films, compounds containing donor-/acceptor groups are admixed with a polymer matrix or bonded to a polymer backbone and can be aligned by means of electrical or magnetic fields.

In addition, it may be advantageous if such polymers, in addition to nonlinear optical properties, also have liquid-crystalline properties. In this respect, reference is made, for example, to EP 262,680 A (published on Apr. 6 1988), U.S. Pat. No. 4,810,338 (published on Mar. 7, 1989), EP 271,730 A (published on Jun. 22, 1988), U.S. Pat. No. 4,779,961 (published on Jul. 5, 1988) from Hoeschst Celanese Co. In these publications, liquid-crystalline polymers having nonlinear optical properties are described. However, high-molecular-weight polymers can usually only be oriented by applying a strong electrical or magnetic field.

It is therefore an object of the present invention to provide compounds which have nonlinear optical properties and can readily be oriented in a simple manner, even without application of electrical or magnetic fields. A further object of the present invention is to provide compounds of the abovementioned type which additionally have liquid-crystalline properties.

SUMMARY OF THE INVENTION

The foregoing objects and others which are apparent from the following description are accomplished in accordance with this invention, generally speaking, by providing cyclic organosiloxanes which contain at least one Si-bonded organic radical which has at least one donor/acceptor $\pi$-electron system, a process for their preparation, and use of the same.

The cyclic organosiloxanes of this invention are preferably those comprising units of the general formula

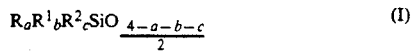
(I)

where R may be the same or different and represents a chiral or achiral, monovalent organic radical which has at least one donor/acceptor $\pi$-electron system; $R^1$ represents the same or different, monovalent, hydrocarbon radicals and monovalent substituted hydrocarbon radicals; $R^2$ may be the same or different and represents a mesogenic radical; a is 0, 1 or 2; b is 0, 1 or 2; and c is 0, 1 or 2 with the proviso that the sum of a, b and c is two, and the cyclic organosiloxane contains at least one radical R.

DETAILED DESCRIPTION OF THE INVENTION

The cyclic organosiloxanes of this invention are preferably those having from 2 to 10 silicon ring atoms.
R is preferably a radical of the formula

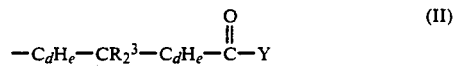
(II)

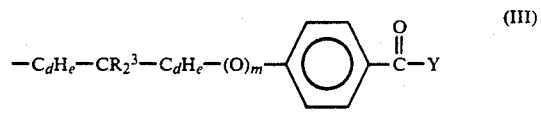
(III)

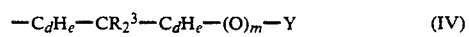
(IV)

or

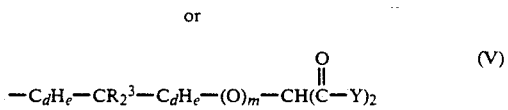
(V)

where $R^3$ may be the same or different and represents a hydrogen atom, a cyano group, a hydroxyl group, a halogen atom or an alkyl group having from 1 to 4 carbon atoms; d in each case represents the same or different integers of from 0 to 12, and preferably from 1 to 6; e in each case represents the same or different integers of from 0 to 24 and preferably from 1 to 12; m is 0 or 1; and Y represents a chiral or achiral radical having a donor/acceptor $\pi$-electron system.

The radical Y preferably has a side chain/axis ratio of from 2:1 to 20:1, preferably from 2:1 to 10:1, and more preferably 10:1.5, with the proviso that the phenylene group is included in the determination of the side chain-/axis ratio in the case where R is a radical of formula (III), and the CO group is included in the determination of the side chain/axis ratio in the case where R is a radical of formula (II) or (V). The side chain/axis ratio here is the ratio of the maximum length to the maximum width of the corresponding crystal structures taking into account the van-der-Waals radii; this ratio can be determined by methods known per se.

The side chain/axis ratio of molecules or molecule parts is preferably determined by minimizing the energy of the corresponding crystal structures without complete conformation analysis, for example using the EDP program "Discover" (Molecular Modeling System, Version 2.5, BIOSYM Technologies, San Diego), and subsequently determining the maximum length and the maximum width, taking into account the van-der-Waals radii, by rotating the crystal structure in the coordinate system. The crystal structures here can be obtained directly or built up from crystal fragments. Thus, crystal structures can be built up, for example, from crystal fragments of the Cambridge Structural Database CSD (Cambridge Crystallographic Data Centre, University Chemical Laboratory, Lensfield Road, Cambridge CB2 1EW, U.K.) using the EDP program "Insight" (Molecular Modeling System, Version 2.5, BIOSYM Technologies, San Diego) and, if necessary, by supplementing this using the residue library of this EDP program.

The radical $R^3$ is preferably a hydrogen atom, a hydroxyl group, a fluorine, chlorine or bromine atom or a methyl or ethyl radical, in which hydrogen, fluorine and the methyl group are the preferred groups.

Preferred radicals represented by Y are nitroaniline radicals, nitrostilbene radicals and unsubstituted or, for example, alkyl- and/or halogen-substituted radicals of the general formulas

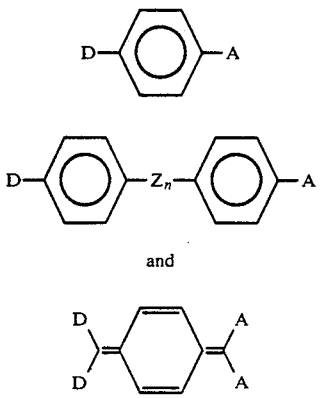

in which A may be the same or different and represents an electron-withdrawing radical, such as, for example, a nitro, cyano, dicyanovinyl, tricyanovinyl, acyl, trifluoromethyl or alkoxysulfonyl group; D may be the same or different and represents an electron-donating radical, such as, for example, a halogen atom or an amino, hydroxyl, mercapto, alkyl, alkoxy, alkylthio, acyloxy or vinyl group; Z represents a conjugated multiple-bond system between the same or different atoms, such as, for example, —CH=CH—, —C≡C—, —CH=N— or —N=N—; and n is an integer of from 0 to 8, preferably from 0 to 2, and more preferably 1, with the proviso that in the radicals Y of the general formulas (VI) to (VIII), a hydrogen atom has been replaced by a chemical bond. The radical Y in the radical R is preferably bonded via D, R and D having one of the abovementioned meanings, D in particular being an amino or hydroxyl group.

Preferred radicals A are nitro, cyano and dicyanovinyl groups.

Preferred radicals D are amino, alkyl, alkoxy, alkylthio and acyloxy groups, in which the amino and alkoxy groups are preferred.

The preferred meanings of Z are —CH=CH—, —CH=N— and —N=N—.

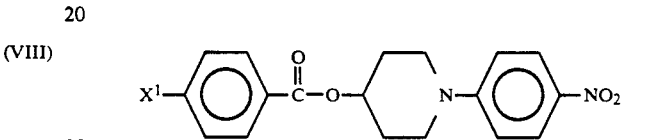

having a side chain/axis ratio of 2.8:1,

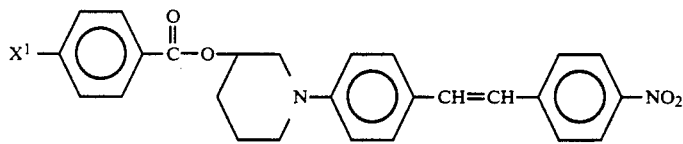

having a side chain/axis ratio of 2.4:1, and

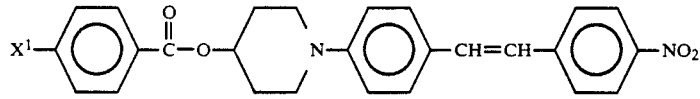

having a side chain/axis ratio of 2.5:1, where $X^1$ has, for example, one of the meanings $(CH_2)_4$—, $(CH_2)_3$—O—, $(CH_2)_5$—O— and $(CH_2)_6$—O—, and

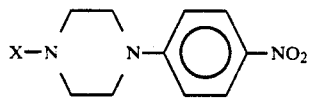

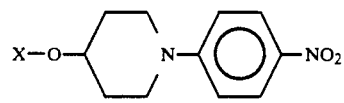

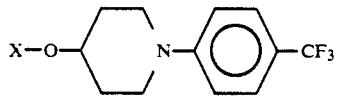

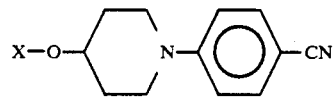

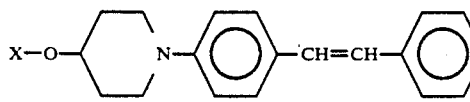

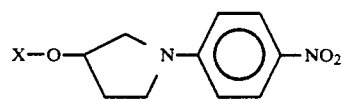

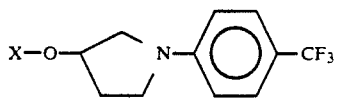

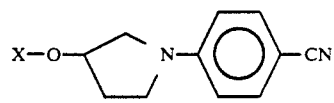

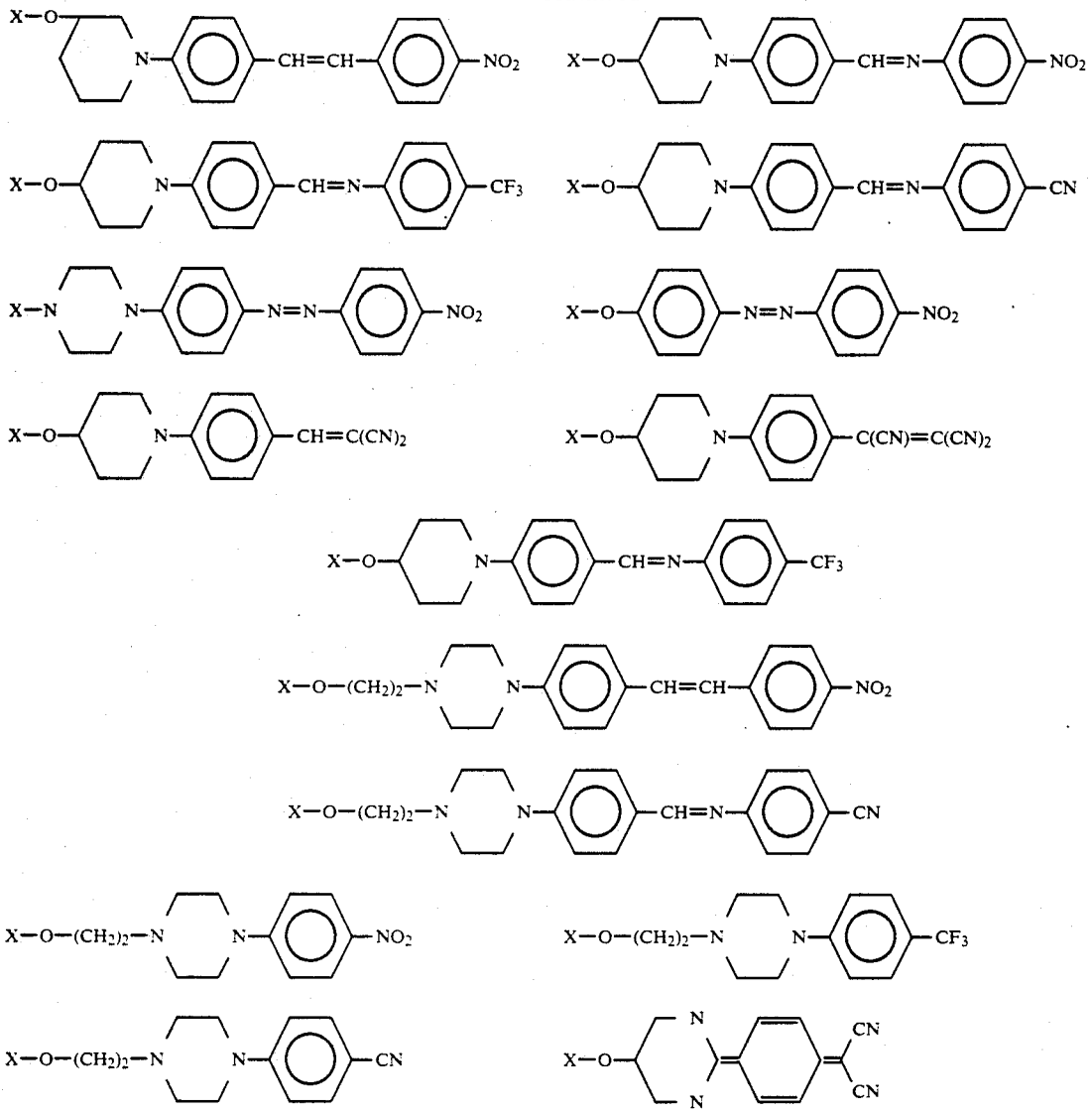

where X has, for example, one of the meanings

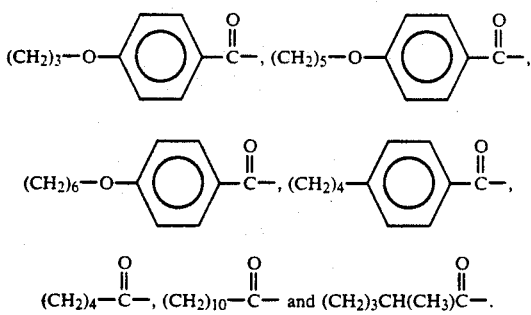

The radical $R^1$ is preferably a monovalent hydrocarbon radical having from 1 to 6 carbon atoms which may be substituted by halogen atoms or hydroxyl groups.

Examples of radicals represented by $R^1$ are the methyl, ethyl, n-propyl, iso-propyl, 1-n-butyl, 2-n-butyl, iso-butyl, tert-butyl, n-pentyl, iso-pentyl, neopentyl, tert-pentyl and n-hexyl radicals, alkenyl radicals, such as the vinyl and allyl radicals, cycloalkyl radicals, such as cyclopentyl and cyclohexyl radicals, and the phenyl radical.

Examples of substituted radicals represented by $R^1$ are cyanoalkyl radicals, such as the β-cyanoethyl radical, and halogenated hydrocarbon radicals, for example haloalkyl radicals, such as the 3,3,3-trifluoro-n-propyl radical, the 2,2,2,2',2',2'-hexafluoropropyl radical, and the heptafluoroisopropyl radical, and haloaryl radicals, such as the o-, m- and p-chlorophenyl radicals and the o-, m- and p-fluorophenyl radicals.

Preferred radicals represented by $R^1$ are the methyl, ethyl and phenyl radicals, and more preferably the methyl radical.

The mesogenic radicals represented by $R^2$ may be any mesogenic groups known heretofore. Mesogenic groups are described, for example, in Dietrich Demus et al, "Flüssige Kristalle in Tabellen" [Liquid Crystals in Tables], VEB Deutscher Verlag für Grundstoffindustrie, Leipzid, Volume I (1974) and Volume II (1984), the groups mentioned therein being included herein by reference.

Examples of mesogenic groups are derivatives of cyclohexane, such as cyclohexyl cyclohexylcarboxylate, phenyl cyclohexylcarboxylate, cyclohexyl phenyl ether, cyclohexylbenzenes, dicyclohexyl derivatives, derivatives of stilbene, cinnamic acid esters and derivatives thereof, phenyl benzoate and derivatives thereof, steroids, such as cholesterol, derivatives thereof, such as cholesterol esters, cholestan and derivatives thereof, benzylideneanilines, azobenzene and derivatives thereof, azoxybenzene and derivatives thereof, alkyl and alkoxy derivatives of biphenyl, and Schiff's bases.

The radicals represented by $R^2$ are preferably radicals of the formulas (II) to (V), where $R^3$, d, e and m are the same as above and Y represents a cholesteryl radical or a radical of the formula

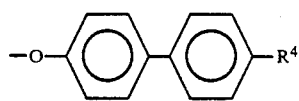
(IX)

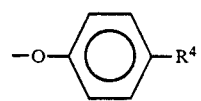
(X)

in which $R^4$ represents a hydrogen atom, a halogen atom, a nitro or cyano group, or an achiral or chiral ester group, or an alkyl, alkoxy, aryl, aryloxy, acyl or acyloxy group, which may be optionally be substituted.

Examples of $R^4$ ar alkyl groups having from 1 to 10 carbon atoms, such as the methyl, ethyl, n-propyl, isopropyl, 1-n-butyl, 2-n-butyl, iso-butyl, tert-butyl, n-pentyl, isopentyl, neopentyl and tert-pentyl radicals, hexyl radicals, such as the n-hexyl radical, heptyl radicals, such as the n-heptyl radical, octyl radicals, such as the n-octyl radical and iso-octyl radicals, such as the 2,2,4-trimethylpentyl radical, nonyl radicals, such as the n-nonyl radical, and decyl radicals, such as the n-decyl radical; cycloalkyl radicals, such as the cyclopentyl, cyclohexyl and cycloheptyl radicals, and methylcyclohexyl radicals, and the corresponding alkoxy groups.

Examples of $R^4$ are aryl radicals, such as the phenyl radical and substituted phenyl radicals, and the corresponding aryloxy radicals.

Further examples of $R^4$ are

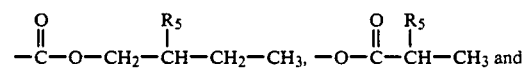

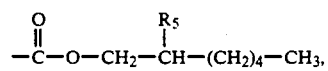

where $R_5$ may be the same or different and represents a hydrogen atom, a chlorine or fluorine atom, or a hydroxyl, cyano or methyl group.

Preferred radicals represented by $R^4$ are hydrogen atoms, cyano and nitro groups, and methyl, methoxy, ethyl, ethoxy, 2-methylbutoxy, 2-methylheptoxy and ester groups, in which hydrogen atoms, cyano and methoxy groups are particularly preferred.

The cyclic organosiloxanes of this invention may be monofunctional cyclic organosiloxanes of polyfunctional cyclic organosiloxanes.

The monofunctional cyclic organosiloxanes are preferably those comprising units of the formula (I) in which R, $R^1$ and $R^2$ are as defined above, and a is 0 or 1, b is 1 or 2, and c is 0, with the proviso that the sum of a and b is two, and the cyclic organopolysiloxane contains the R radical.

The monofunctional cyclic organosiloxanes of this invention preferably contain 2 and 8, and more preferably 3 to 5, silicon ring atoms.

Examples of monofunctional cyclic organosiloxanes of this invention are

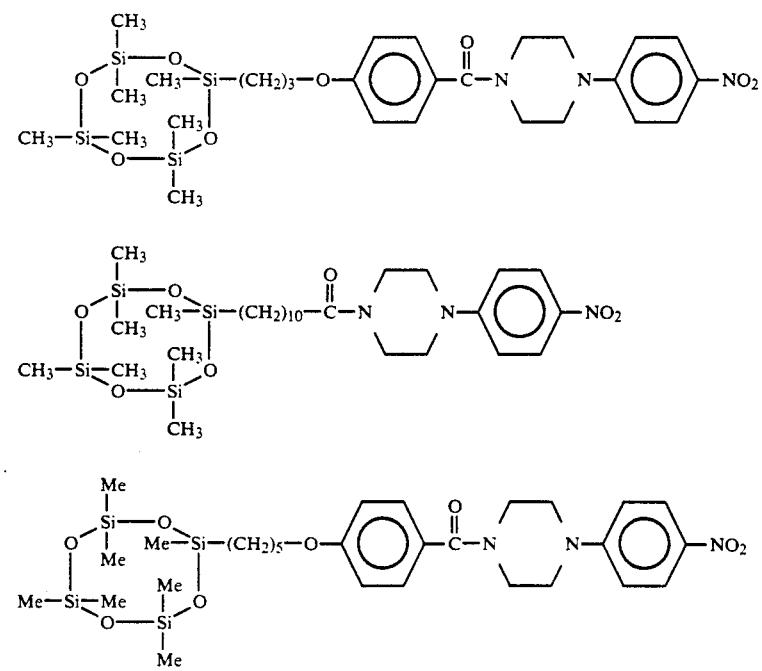

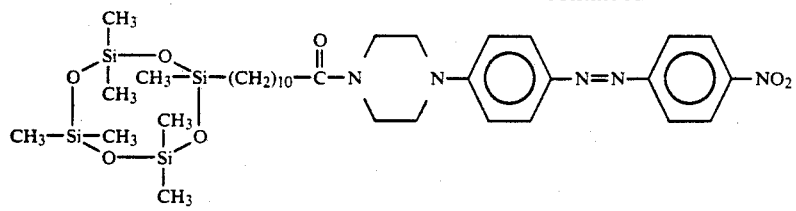

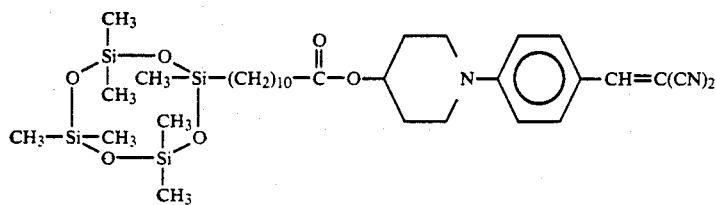

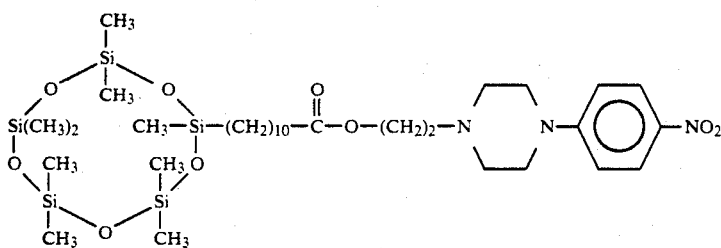

The polyfunctional cyclic organosiloxanes are preferably those comprising units of the formula (I) where R, $R^1$, $R^2$, a, b and c are the same as above, with the proviso that the sum of a, b and c is two, and the cyclic organosiloxane contains at least one R radical and at least one further radical selected from the group consisting of R and $R^2$. The cyclic organosiloxane preferably has mesogenic properties.

The polyfunctional cyclic organosiloxanes of this invention preferably contain 3 to 7 silicon ring atoms.

Examples of polyfunctional organosiloxanes of this invention are

-continued

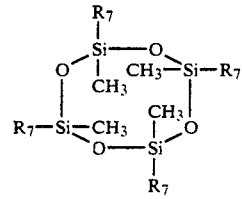

where $R_7$ is

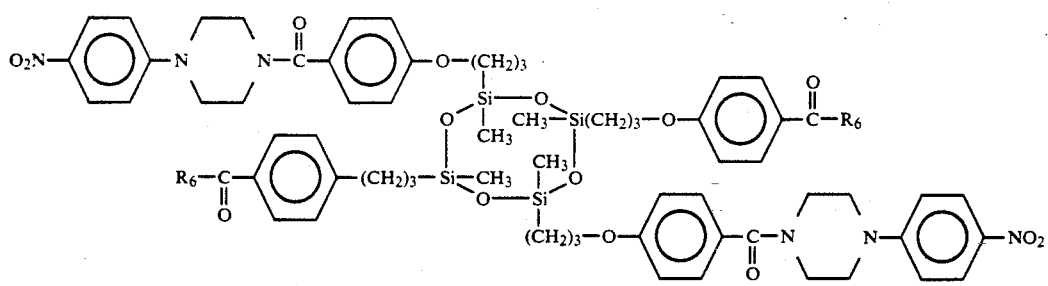

there $R_6$ is a cholesteryl radical or

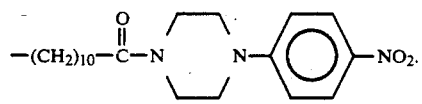

The cyclic organosiloxanes of this invention can be prepared by processes known per se. Thus, cyclic organosiloxanes comprising units of the formula (I) can preferably be prepared by reacting cyclic organosiloxanes containing at least one Si-bonded hydrogen atom, in particular, those having units of the formula

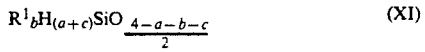

where $R^1$, a, b and c are the same as above, with the proviso that the sum of a, b and c is 2, with chiral or achiral compounds which have at least one donor-acceptor π-electron system, preferably a donor-acceptor π-electron system having a side chain/axis ratio between 2:1 and 20:1, and contain an aliphatic multiple bond, preferably a terminal aliphatic multiple bond, and in particular those of the formulas

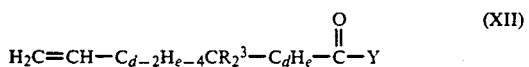

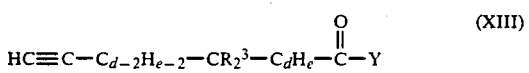

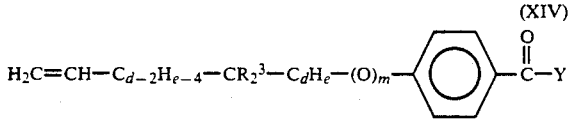

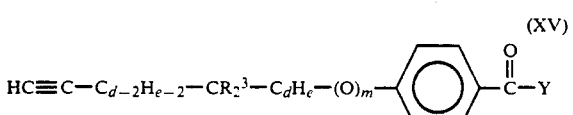

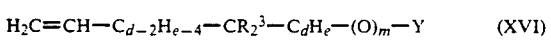

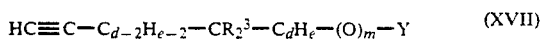

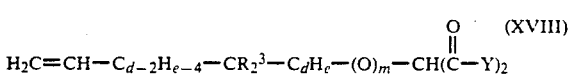

or

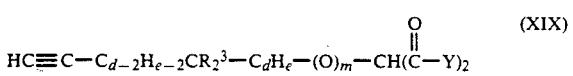

where $R^3$, d, e, m and Y are the same as above, and, if appropriate, with mesogenic compounds containing an aliphatic multiple bond, preferably a terminal, aliphatic multiple bond.

In the process of this invention, the cyclic organosiloxanes containing at least one Si-bonded hydrogen atom and comprising units of formula (XI) are preferably those which contain 2 to 10 silicon ring atoms.

The cyclic organosiloxanes having at least one Si-bonded hydrogen atom which are employed in the process of this invention are commercial products or can be prepared by methods which are known in silicon chemistry. In this respect, reference is made, for example, to W. Noll, "Chemistry and Technology of Silicones", Academic Press, Orlando, 1968, pages 190 ff., and M. wick, G. Kreis, F.-H. Kreuzer, "Silicones", in "Ullmanns Encyclokpädie der tecnhischen Chemie" [Ullmann's Encyclopedia of Industrial Chemistry], Verlag Chemie, Weinheim, 4th Edition, 1982, Vol. 21, pages 511 ff.

The chiral or achiral compounds which have at least one donor-acceptor π-electron system and an aliphatic multiple bond and employed in the process of this invention are commercial products or can be prepared by methods which are known in organic chemistry. In this respect, reference is made, for example, to E. C. Taylor, J. S. Skotnicki, Synthesis (1981) 606.

Preferably, approximately (a) equivalents of compounds of formulas (XII) to (XIX) and approximately (c) equivalents of mesogenic compounds containing an aliphatic multiple bond are employed.

In the process of this invention, each component may be an individual type of this component or a mixture of at least two different types of this component.

In the process of this invention, a compound or compounds containing units of formula (XI) may first be reacted with a compound or compounds of formula (XII) to (XIX) and then with one or more mesogenic compounds containing an aliphatic multiple bond, or vice versa. All components are preferably reacted with one another in one step.

The reactions are preferably carried out in the presence of a catalyst.

In the process of this invention, the catalysts employed may be the same as those employed heretofore for the addition of Si-bonded hydrogen atoms with aliphatic multiple bonds. These are principally metals of sub-group 8 and inorganic and organic compounds thereof, in which platinum, and complexes thereof are preferred.

Examples of such catalysts are finely divided elemental platinum supported on an inert carrier, such as activated charcoal, $SiO_2$ or $Al_2O_3$, as in U.S. Pat. No. 2,970,150 (D. L. Bailey, Union Carbide Corporation; published on Jan. 31, 1961), hexachloroplatinic acid, as in U.S. Pat. No. 2,823,218 (J. L. Speier, Dow Corning Corporation; published on Feb. 11, 1958), and derived therefrom, chloroplatinates, platinum complexes of the type $L \cdot PtCl_2$, where L represents a linear or cyclic monoolefin, such as ethene, propene and cyclohexene, as in U.S. Pat. No. 3,159,601 and U.S. Pat. No. 3,159,662 (Bruce A. Ashby, General Electric Company; each published on Dec. 1, 1964), platinum complexes of the type $L \cdot PtCl_2$, where L represents a cyclic diolefin, such as 1,5-cyclooctadiene, norbornadiene or cyclopentadiene, as in Japanese Preliminary Published Specification 69/76,529 and Japanese Preliminary Published Specification 79/76,530 (Masatoshi Arai, Shin-Etsu Chemical Industry Co, Ltd.; each published on Jun. 19, 1979) and U.S. Pat. No. 4,276,252 (G. Kreis, Wacher-Chemic GmbH, published on Jun. 30, 1981) or a cyclic polyolefin, as in the German application with the file reference P 39 06 514.6 (G. Wenski, Consortium für elektrochemische Industrie GmbH; filed on Mar. 1, 1989), platinum vinylsiloxane complexes, as in U.S. Pat. No. 3,814,730 (B. D. Karstedt, General Electric Company; published on Jun. 4, 1974), and acetylacetonate complexes of platinum, as in U.S. Pat. No. 4,177,341 (G. Kreis, Consortium für elektrochemische Industrie GmbH; published on Dec. 4, 1979).

Due to their effectiveness, platinum complexes of the type $L \cdot PtCl_2$ where L represents a cyclic diolefin or polyolefin, in particular dicyclopentadienylplatinum dichloride, are preferably employed in the process of this invention.

The catalyst employed in this invention may be an individual type of catalyst or a mixture of at least two different types of such catalysts.

The amounts of catalyst employed in the process of this invention may be the same as employed int he processes known heretofore for the addition reaction of Si-bonded hydrogen with an aliphatic multiple bond in the presence of a catalyst. These are preferably from 0.1 to 1,000 ppm by weight, and more preferably from 2 to 400 ppm by weight, calculated as elemental platinum, and based on the total weight of the reaction composition.

The process of this invention can be carrier out in the presence or absence of solvents, the use of organic solvents which are inert to the reaction composition being preferred.

Examples of solvents are alcohols, such as methanol, ethanol, n-propanol, iso-propanol, n-, sec-, tert-butanol and 2-butanol; esters, such as methyl acetate, ethyl acetate, n- and iso-propyl acetate, n-, sec- and tert-butyl acetate, ethyl formate and diethyl carbonate; ethers, such as dioxane, tetrahydrofuran, diethyl ether, di-n-propyl ether, diisopropyl ether, di-n-butyl ether and anisole; chlorinated hydrocarbons, such as dichloromethane, trichloromethane, tetrachloromethane, 1,2-dichloroethane, 1,1,1-trichloroethane, trichloroethylene, tetrachloroethylene and chlorobernzene; hydrocarbons, such as pentane, n-hexane, mixtures of isomers, cyclohexane, heptane, octane, ligroin, petroleum ether, benzene, ethylbenzene, toluene and xylenes, and ketones, such as acetone, methyl ethyl ketone and methyl isobutyl ketone, or mixtures of these solvents, in which toluene, dichloromethane and tetrahydrofuran are preferably employed.

The term solvent does not mean that all the reaction components must be soluble therein. The reaction can also be carried out in a suspension or emulsion of one or more of the reactants.

The temperatures and pressures used in the process of this invention may be the same as used in the processes known heretofore for the addition reaction of Si-bonded hydrogen with an aliphatic multiple bond in the presence of a catalyst. These are preferably temperatures of from 0 to 200° C. and pressures of from 900 to 1,100 hPa, in which temperatures of from 20° to 120° C. are preferred. If desired, higher or lower pressures can also be used.

It is, of course, possible in the process of this invention, for the reaction composition to contain substances in addition to a cyclic organosiloxane having at least one hydrogen atom, chiral or achiral compounds having at least one donor/acceptor $\pi$-electron system and containing a terminal aliphatic multiple bond, optionally a mesogenic compound containing a terminal aliphatic multiple bond, catalyst and optionally solvent.

The reaction time depends, inter alia, on the reaction temperature, and on the activity and amount of the catalyst used. It is generally from about 20 minutes to about 24 hours.

The cyclic organosiloxanes of this invention having nonlinear optical properties, and in particular the cyclic organosiloxanes having both nonlinear optical properties and liquid-crystalline properties, have the advantage that they form transparent films which can very easily be oriented by simple mechanical treatment. This oriented state can be frozen by quenching below the glass point and gives a clear film. It is, of course, also possible to use conventional methods such as surface effects, or electrical or magnetic fields for orientation.

In addition, the cyclic organosiloxanes of this invention exhibit both high mechanical stability and high thermal oxidative stability.

In addition, the cyclic organosiloxanes of this invention, due to their relatively low molecular weight compared with high-molecular-weight polymers, have relatively low viscosity and good solubility in conventional solvents, such as tetrahydrofuran, which is advantageous for their processibility. This also provides the possibility of mixing the cyclic organosiloxanes of this invention in a relatively simple manner, conforming to the particular application, with other, in particular structurally similar, components, and makes it possible to vary the concentration of the cyclic organosiloxanes of this invention over a broad range.

The process of this invention has the advantage that the properties of the cyclic organosiloxanes of this invention can be adjusted in a relatively simple manner, and very specifically, conforming to set demands. Thus, for example, cyclic organosiloxanes having nonlinear optical properties and having nonlinear optical properties in combination with smectic, nematic or cholesteric liquid-crystalline properties can be prepared.

The cyclic organosiloxanes of this invention can be used for all purposes for which compounds having nonlinear optical properties of having nonlinear optical properties in combination with liquid-crystalline properties have been or could have been employed heretofore. Thus, for example, they can be used in microelectronics, data transfer or communications technology, in computer technology, in displays, optical switches, optical information stores and integrated circuits, and for medical applications.

In the examples described below, all parts and percentages are by weight, unless otherwise specified. If not stated otherwise, the examples below are carried out at the pressure of the ambient atmosphere, i.e., at about 1,000 hPa, and at room temperature, i.e., at about 23° C., or at a temperature established on combining the reactants at room temperature without additional heating or cooling.

The glass transition temperatures and the clear point of the cyclic organosiloxanes of this invention are in each case determined by differential thermoanalysis (DTA). The purity is determined by gel-permeation chromatography (GPC).

EXAMPLE 1

About 0.1 ml of a 1 percent solution of dicyclopentadeienylplatinum dichloride in dichloromethane, prepared by methods known from the literature, such as, for example, J. Chatt, L. M. Vallarino, L. M. Venanzi, J. Chem. Soc. (London) (1957) 2496–505 and H. C. Clark, L. E. Manzer, J. Organometal. Chem. 59 (1973) 411–28, is added to a solution containing 3.0 g of 1-(4-(2-allyloxy)benzoyl)-4-(4-nitrophenyl)piperazine of the structural formula

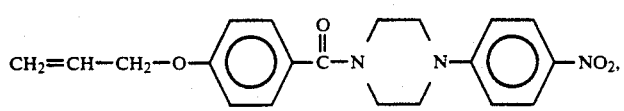

2.5 g of heptamethylhydrogencyclotetrasiloxane and 15 ml of anhydrous toluene, and the resultant mixture is refluxed for 3 hours. In order to separate off the platinum-containing, fine precipitates, the mixture is filtered through a short column packed with silica gel. The solvents are subsequently removed by distillation under reduced pressure, and the residue is dissolved in tetrahydrofuran. The reaction product is precipitated by adding ethanol, filtered off and dried under reduced pressure at a temperature of 60° C. About 4.4 g of a yellowish solid are obtained, which according to GPC, has a purity of 95.1 percent. This substance is applied to a microscope slide and warmed to above the melting point, and the melt is re-cooled and oriented just below the melting point by gentle pressure and mechanical shear after application of a cover slip. At room temperature, the substance forms a transparent film having a smectic C phase, which clears at a temperature of 44.8° C. The glass point is 10° C.

EXAMPLE 2

About 0.05 ml of the 1 percent dicyclopentadienylplatinum dichloride solution described in Example 1 is added to a solution containing 1.0 g of 1-(4-(2-allyloxy)-benzoyl)-4-(4-nitrophenyl-piperazine of the structural formula

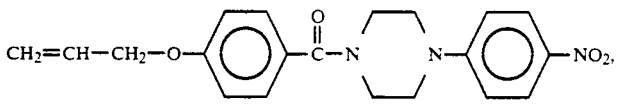

1.5 g of cholesteryl 4-allyloxybenzoate, 0.5 g of pentamethylpentahydrogencyclopentasiloxane and 7.5 ml of anhydrous toluene. The procedure described in Example 1 is repeated using the resultant mixture, with the difference that the product is reprecipitated twice using tetrahydrofuran and ethanol. About 0.4 g of a red solid is obtained, which, according to GPC, has a purity of 96.4 percent. After the preparation described in Example 1, this substance forms, at room temperature, a transparent film having a smectic C phase, and there is a transition to a smectic A phase at a temperature between 184° and 188° C., and it clears between 204° and 238° C. The glass point is 41° C.

EXAMPLE 3

About 0.06 ml of the 1 percent dicyclopentadienylplatinum dichloride solution described in Example 1 is added to a solution containing 2.0 g of 1-(dec-9-enylcarbonyl)-4-(4-nitrophenyl)piperazine of the structural formula

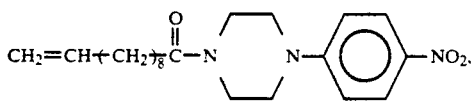

1.3 g of heptamethylhydrogencyclotetrasiloxane and 9 ml of anhydrous toluene. The procedure described in Example 1 is repeated using the resultant mixture. About 2.0 g of a viscous, yellow oil are obtained, which, according to GPC, ha a purity of 100 percent. After the preparation described in Example 1, this substance forms, at room temperature, a transparent, yellow film having a smectic A phase, which clears at a temperature between 57° and 58° C. The glass point is 0° C.

EXAMPLE 4

About 0.05 ml of the 1 percent dicyclopentadienylplatinum dichloride solution described in Example 1 is added to a solution containing 1.5 g of N-(N'-(dec-9-enylcarbonyl)piperazinyl)-4-(4'-nitro)azobenzene of the structural formula

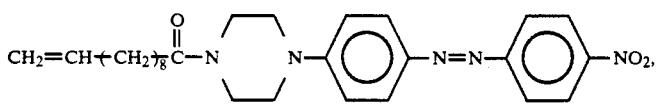

1.0 g of heptamethylhydrogencyclotetrasiloxane and 8 ml of anhydrous toluene. The procedure described in Example 1 is repeated using the resultant mixture. About 1.0 g of a dark red solid is obtained, which, according to GPC, has a purity of 100 percent. After the preparation described in Example 1, this substance forms, at room temperature, a clear film which exhibits several different smectic phases below the clearing point at 179° C.

EXAMPLE 5

About 0.05 ml of the 1 percent dicyclopentadienylplatinum dichloride solution described in Example 1 is added to a solution containing 1.5 g of 1-(4-(pent-4-enyloxy)benzoyl)-4-(4-nitrophenyl)piperazine of the structural formula

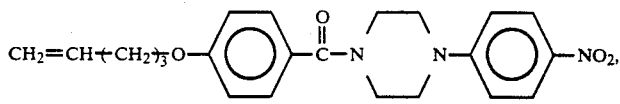

1.2 g of heptamethylhydrogencyclotetrasiloxane and 7 ml of anhydrous toluene. The procedure described in Example 1 is repeated using the resultant mixture. About 1.7 g of a yellow solid are obtained, which, according to GPC, has a purity of 100 percent. After the preparation described in Example 1, the substance forms, at room temperature, a transparent, yellow film having a smectic C phase, which undergoes a transition to a smectic A phase at a temperature of 36° C. and clears between 79° and 115° C. The glass point is 5° C.

EXAMPLE 6

About 0.05 ml of the 1 percent dicyclopentadienylplatinum dichloride solution described in Example 1 is added to a solution containing 1.5 g of 1-(2,2- dicyanovinyl)phenyl)-4-(dec-9-enylcarbonyloxy)piperizine of the structural formula

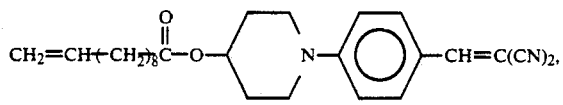

1.1 g of heptamethylhydrogencyclotetrasiloxane and 7 ml of anhydrous toluene. The procedure described in Example 1 is repeated using the resultant mixture. About 2.2 g of a yellow solid are obtained, which, according to GPC, has a purity of 97.4 percent. After the preparation described in Example 1, this substance forms, at room temperature, a transparent, yellow film which tends toward crystallization, having a smectic A phase, which clears at a temperature of 50° C.

EXAMPLE 7

About 0.04 ml of the 1 percent dicyclopentadienylplatinum dichloride solution described in Example 1 is added to a solution containing 2.0 g of 1-(dec-9-enylcarbonyl)-4-(4-nitrophenyl)piperazine of the structural formula

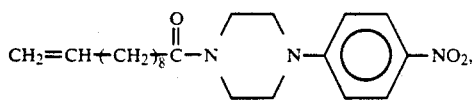

0.26 g of tetramethyltetrahydrogencyclotetrasiloxane and 6 ml of anhydrous toluene. The procedure described in Example 1 is repeated using the resultant mixture. About 1.2 g of a yellow solid are obtained, which, according to GPC, has a purity of 99.8 percent. After the preparation described in Example 1, this substance forms, at room temperature, a transparent, yellow film having a smectic A phase, which clears at a temperature between 97.5° and 99.8° C. The glass point is 27° C.

What is claimed is:

1. A cyclic organosiloxane which contains at least one Si-bonded organic radical which has at least one donor/acceptor $\pi$-electron system.

2. The cyclic organosiloxane of claim 1, wherein the cyclic organosiloxane has units of the formula

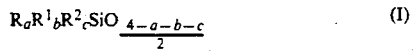

in which R is selected from the group consisting of a chiral monovalent organic radical which has at least one donor/acceptor $\pi$-electron system and an achiral monovalent organic radical which has at least one donor/acceptor $\pi$ electron system; $R^1$ is selected from the group consisting of a monovalent hydrocarbon radical and a substituted monovalent hydrocarbon radical; $R^2$ is a mesogenic radical; a is 0, 1 or 2; b is 0, 1 or 2; and c is 0, 1 or 2 with the proviso that the sum of a, b and c is two, and the cyclic organosiloxane contains at least one R radical.

3. The cyclic organosiloxane of claim 2, in which R is a radical selected from the group consisting of the formulas

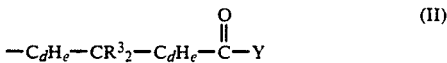

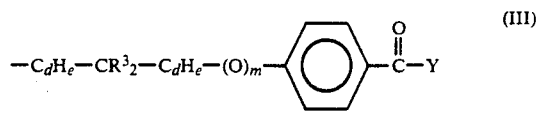

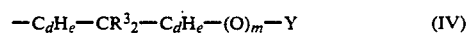

and

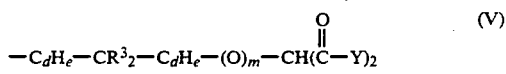

in which $R^3$ is selected from the group consisting of a hydrogen atom, a cyano group, a hydroxyl group, a halogen atom and an alkyl group having from 1 to 4 carbon atoms; d is an integer of from 0 to 12; e is an integer of from 0 to 24; m is 0 or 1; and Y is selected from the group consisting of a chiral monovalent organic radical having a donor/acceptor $\pi$-electron system and an achiral monovalent organic radical having a donor/acceptor $\pi$-electron system 4. The cyclic organosiloxane of claim 3, in which Y is selected from the group consisting of a nitroaniline radical, a nitrostilbene radical, an unsubstituted and substituted radical of the formula

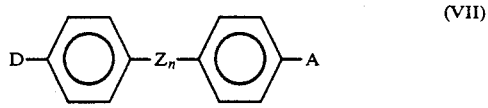

and

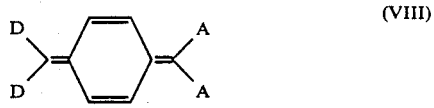

in which A is an electron-withdrawing radical; D is an electron-donating radical; Z is a conjugated multiple-bond system; and n is an integer of from 0 to 8, with the proviso that, in the radicals Y of the formulas (VI) to (VIII), a hydrogen atom has been replaced by a chemical bond.

5. The cyclic organosiloxane of claim 3, wherein the radical Y has a side chain/axis ratio of from 2:1 to 20:1, with the proviso that the phenylene group is included in the determination of side chain/axis ratio in the case where R is a radical of formula (III), and the CO group is included in the determination of the side chain/axis ratio in the case where R is a radical of formula (II) or (V).

6. The cyclic organosiloxane of claim 5, in which Y is selected from the group consisting of a nitroaniline radical, a nitrostilbene radical and an unsubstituted or substituted radical of the formula

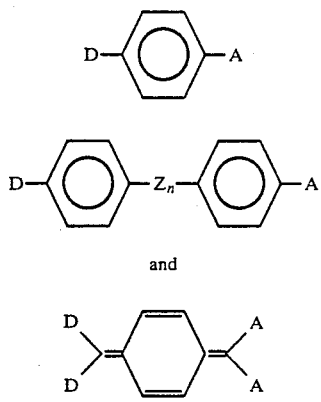

(VI)

(VII)

and

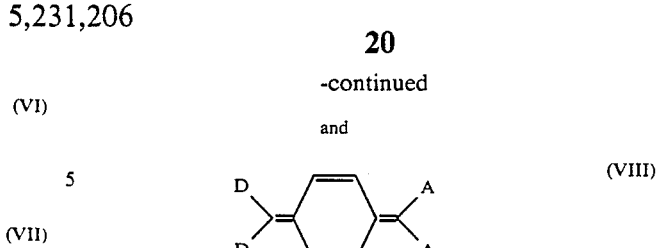

(VIII)

in which A is an electron-withdrawing radical; D is an electron-donating radical; Z is a conjugated multiple-bond system; and n is an integer of from 0 to 8, with the proviso that, in the radicals Y of the formulas (VI) to (VIII), a hydrogen atom has been replaced by a chemical bond.

10. The cyclic organosiloxane of claim 7, in which the radical Y has a side chain/axis ratio of from 2:1 to 20:1, with the proviso that the phenylene group is included in the determination of side chain/axis ratio in the case where R is a radical of formula (III), and the CO group is included in the determination of the side chain/axis ratio in the case where R is a radical of formula (II) or (V).

11. The cyclic organosiloxane of claim 10, in which Y is selected from the group consisting of a nitroaniline radical, a nitrostilbene radical, an unsubstituted and substituted radical of the formula in which A is an electron-withdrawing radical; D is an electron-donating radical; Z is a conjugated multiple-bond system; and n is an integer of from 0 to 8, with the proviso that, in the radicals Y of the formulas (VI) to (VIII), a hydrogen atom has been replaced by a chemical bond.

7. The cyclic organosiloxane of claim 2, which contains from 2 to 10 silicon ring atoms.

8. The cyclic organosiloxane of claim 7, in which R is a radical selected from the group consisting of the formulas

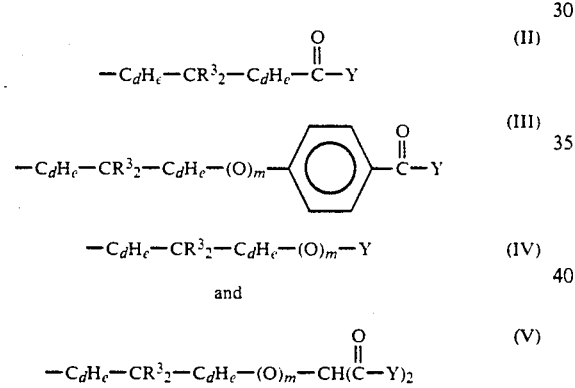

in which $R^3$ is selected from the group consisting of a hydrogen atom, a cyano group, a hydroxyl group, a halogen atom and an alkyl group having from 1 to 4 carbon atoms; d is an integer of from 0 to 12; e is an integer of from 0 to 24; m is 0 or 1; and Y is selected from the group consisting of a chiral monovalent organic radical having a donor/acceptor $\pi$-electron system and an achiral monovalent organic radical having a donor/acceptor $\pi$-electron system.

9. The cyclic organosiloxane of claim 8, in which Y is selected from the group consisting of a nitroaniline radical, a nitrostilbene radical, an unsubstituted and substituted radical of the formula

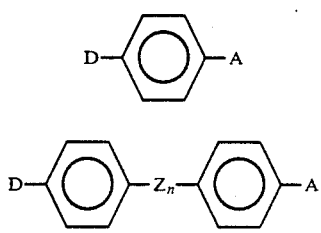

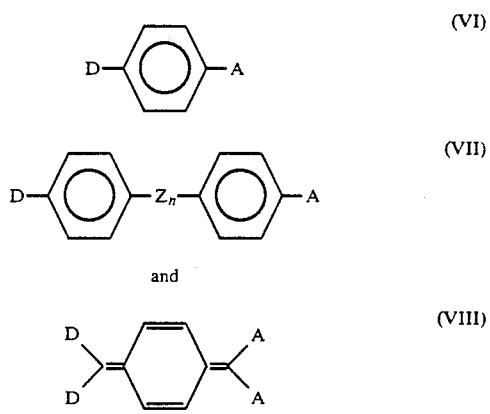

12. The cyclic organosiloxane of claim 1, which contains from 2 to 10 silicon ring atoms.

13. The cyclic organosiloxane of claim 12, in which R is a radical selected from the group consisting of the formulas

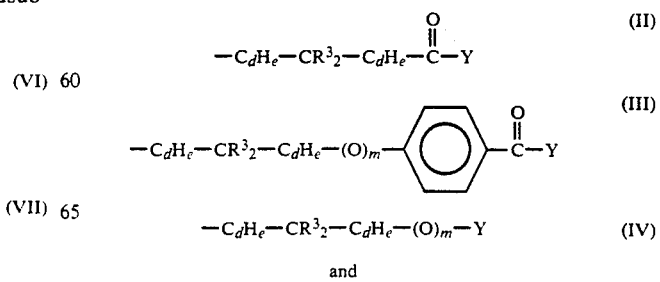

and

-continued

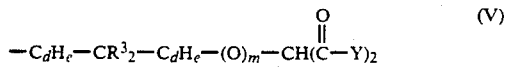    (V)

in which $R^3$ is selected from the group consisting of a hydrogen atom, a cyano group, a hydroxyl group, a halogen atom and an alkyl group having from 1 to 4 carbon atoms; d is an integer of from 0 to 12; e is an integer of from 0 to 24; m is 0 or 1; and Y is selected from the group consisting of a chiral monovalent organic radical having a donor/acceptor $\pi$-electron system and an achiral monovalent organic radical having a donor/acceptor $\pi$-electron system.

14. The cyclic organosiloxane of claim 13, in which the radical Y has a side chain/axis ratio of from 2:1 to 20:1, with the proviso that the phenylene group si included in the determination of side chain/axis ratio in the case where R is a radical of formula (III), and the CO group is included in the determination of the side chain/axis ratio in the case where R is a radical of the formula (II) or (V).

15. The cyclic organosiloxane of claim 14, in which Y is selected from the group consisting of a nitroaniline radical, a nitrostilbene radical, an unsubstituted andsubstituted radical of the formula

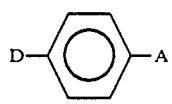    (VI)

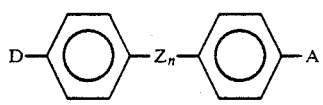    (VII)

and

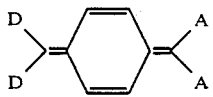    (VIII)

in which A is an electron-withdrawing radical; D is an electron-donating radical; Z is a conjugated multiple-bond system; and n is an integer of from 0 to 8, with the proviso that, in the radicals Y of the formulas (VI) to (VIII), a hydrogen atom has been replaced by a chemical bond.

16. The cyclic organosiloxane of claim 13, in which Y is selected from the group consisting of a nitroaniline radical, a nitrostilbene radical, an unsubstituted andsubstituted radical of the formula

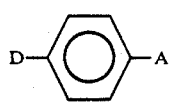    (VI)

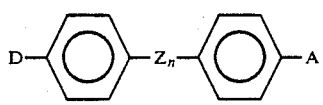    (VII)

and

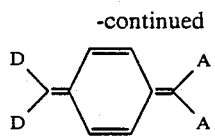    (VIII)

in which A is an electron-withdrawing radical; D is an electron-donating radical; Z is a conjugated multiple-bond system; and n is an integer of from 0 to 8, with the proviso that, in the radicals Y of the formulas (VI) to (VIII), a hydrogen atom has been replaced by a chemical bond.

17. A process for preparing the cyclic organosiloxane of claim 1, which comprises reacting a cyclic organosiloxane containing at least one Si-bonded hydrogen atom with a compound selected from the group consisting of a chiral compound which has at least one donor/acceptor $\pi$-electron system and contains aliphatic unsaturation and an achiral compound which has at least one donor/acceptor $\pi$-electron system and contains aliphatic unsaturation.

18. The process of claim 17, wherein the cyclic organosiloxane containing at least one Si-bonded hydrogen atom is reacted with a compound selected from the group consisting of a chiral compound which has at least one donor/acceptor $\pi$-electron system and contains aliphatic unsaturation and an achiral compound which has at least one donor/acceptor $\pi$-electron system and contains aliphatic unsaturation and with a mesogenic compound containing an aliphatic multiple bond.

19. The process of claim 17, wherein the cyclic organosiloxane containing at least one Si-bonded hydrogen atom has units of the formula

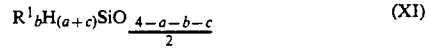    (XI)

where $R^1$ is selected from the group consisting of a monovalent, hydrocarbon radical and a substituted monovalent hydrocarbon radical; a is 0, 1 or 2; b is 0, 1 or 2; and c is 0, 1 or 2, with the proviso that the sum of a, b and c is two.

20. The process of claim 17, wherein the chiral compound which has at least one donor/acceptor $\pi$-electron system and contains aliphatic unsaturation or the achiral compound which has at least one donor/acceptor $\pi$-electron system and contains aliphatic unsaturation is selected from the group consisting of one of the formulas

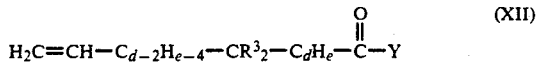    (XII)

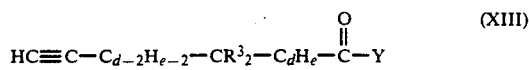    (XIII)

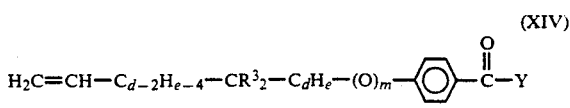    (XIV)

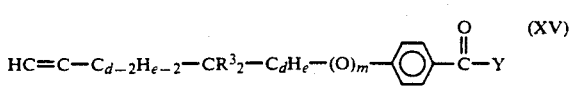    (XV)

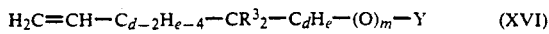    (XVI)

-continued

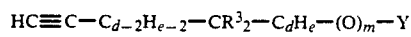

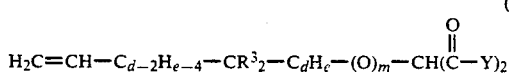

and

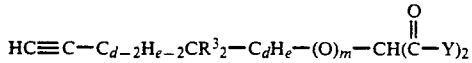

in which $R^3$ is selected from the group consisting of a hydrogen atom, a cyano group, a hydroxyl group, a halogen atom and an alkyl group having from 1 to 4 carbon atoms; d is an integer of from 0 to 12; e is an integer of from 0 to 24; m is 0 or 1; and Y is selected from the group consisting of a chiral monovalent organic radical having a donor/acceptor $\pi$-electron system and an achiral monovalent organic radical having a donor/acceptor $\pi$-electron system.

21. A composition which has nonlinear optical properties and contains a cyclic organosiloxane which is prepared by the process of claim 17.

22. A cyclic organopolysiloxane having non-linear optical properties which is obtained from the reaction of a cyclic organosiloxane containing at least one Si-bonded hydrogen atom with a compound selected from the group consisting of a chiral compound which has at least one donor/acceptor $\pi$-electron system and contains aliphatic unsaturation and an achiral compound which has at least one donor/acceptor $\pi$-electron system and contains aliphatic unsaturation and a mesogenic compound having aliphatic unsaturation.

* * * * *